United States Patent [19]

Cunningham

[11] 4,020,836

[45] May 3, 1977

[54] APPARATUS FOR MEDICAL INJECTIONS

[76] Inventor: James Robert Cunningham, USAF Hospital, PACAF, Box 4363, APO San Francisco, Calif. 96323

[22] Filed: Oct. 23, 1975

[21] Appl. No.: 625,171

Related U.S. Application Data

[63] Continuation-in-part of Ser. No. 577,324, May 14, 1975, and a continuation-in-part of Ser. No. 577,322, May 14, 1975, abandoned.

[52] U.S. Cl. ................................. 128/216; 128/221
[51] Int. Cl.² ......................................... A61M 5/00
[58] Field of Search ............... 128/216, 215, 218 R, 128/218 M, 218 D, 218 DA, 276, 221, 2 F

[56] References Cited

UNITED STATES PATENTS

| | | | |
|---|---|---|---|
| 2,655,919 | 10/1953 | Goodstein et al. | 128/218 D |
| 2,688,967 | 9/1954 | Huber | 128/218 D |
| 2,693,184 | 11/1954 | Lockhart | 128/218 D |
| 3,192,925 | 7/1965 | Cunningham | 128/216 |
| 3,706,305 | 12/1972 | Berger et al. | 128/276 X |
| 3,736,932 | 6/1973 | Satchell | 128/218 R |
| 3,820,542 | 6/1974 | Hurschman | 128/218 DA |

*Primary Examiner*—John D. Yasko
*Attorney, Agent, or Firm*—Paul & Paul

[57] ABSTRACT

,1 A method and apparatus for the administration of medical injections. After insertion of an injection needle into a patient, a negative pressure differential is applied to the exposed end of the injection needle so that if the injection needle has been inserted into any artery or a vein, blood will be drawn up into the needle. A transparent window allows the person administering the injection to observe whether any blood has been drawn into the needle.

1 Claim, 4 Drawing Figures

U.S. Patent    May 3, 1977    4,020,836
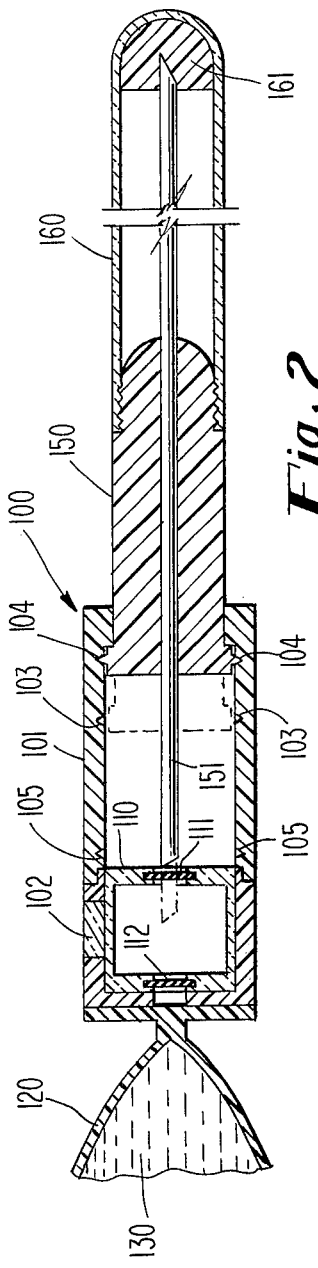
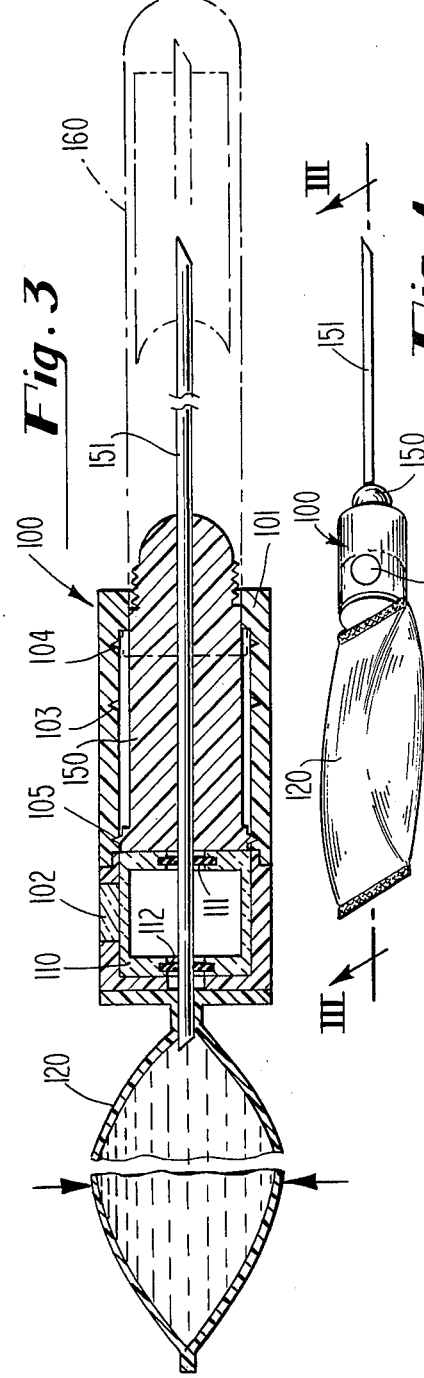
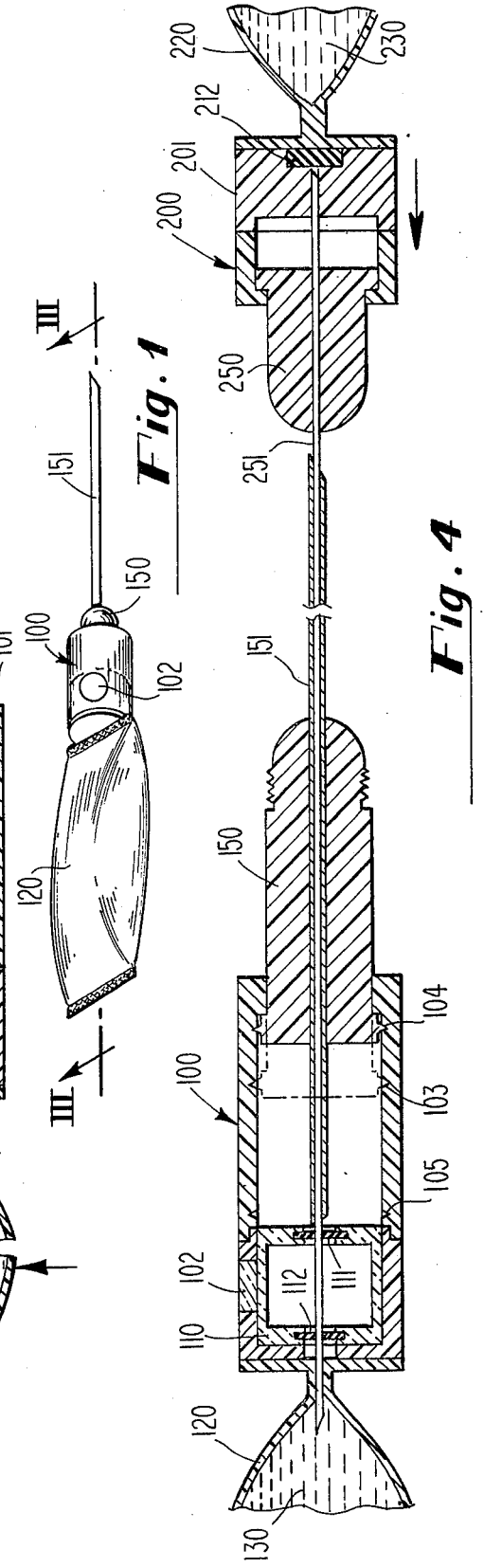

APPARATUS FOR MEDICAL INJECTIONS

REFERENCE TO EARLIER APPLICATIONS

This application is a continuation-in-part of two earlier applications of mine:
1. Ser. No. 577,324 Filed May 14, 1975 for MIXING DISPENSER APPARATUS now abandoned.
2. Ser. No. 577,322, Filed May 14, 1975 for DISPENSING DEVICE.

The disclosures of these two applications are hereby incorporated by reference into this disclosure.

BACKGROUND OF THE INVENTION

In the art directed to disposable syringes, it is known to provide a collapsable container for expressing medicines and the like through a needle, into humans or animals, for example. In my earlier U.S. Pat. No. 3,192,925, a previous development of mine set forth many of the parameters and utilities for devices of this type.

In administering medical injections it is frequently impossible to determine the precise location of the tip of the injection needle after it has been inserted into a patient. In many instances it is important to know whether the tip of the needle has lodged in a vein or an artery. In a conventional hypodermic syringe and needle, it has been a practice for some time for the person administering the injection to withdraw the plunger of the hypodermic syringe after the needle has been inserted into a patient to determine whether any blood wells up into the syringe. If the medication in the syringe is intended to be administered intravenously, the blood welling into the syringe indicates that the tip of the injection needle has lodged in a desired location- either an artery or a vein. If the intent was to deliver the medication into the muscle or subcutaneously, the person administering the injection would withdraw the injection needle and insert it into the patient in another location.

Prior Art disposable syringes are so constructed that it is not possible to create a negative pressure differential on the end of the injection needle to facilitate the withdraw of blood from the patient. In such syringes, the medication is expressed into the patient by squeezing a container which is configured much like the conventional tooth paste tube. Accordingly, it is not possible to manipulate the container itself to create a negative pressure within the container.

THE PRESENT INVENTION

The present invention is therefore principally addressed to providing a dispensing container of the syringe type which is adapted to facilitate determining whether the injection needle has lodged in an artery or vein of the patient to whom an injection is being administered.

To this end, a sealed chamber within the body of the syringe maintains a negative pressure differential which is applied to the end of the injection needle when said end is inserted into the chamber by penetrating a sealed orifice in the wall of the chamber. The sealed chamber has a transparent window to allow the person administering the injection to determine whether or not blood has welled up into the needle after the lower differential pressure has been applied to the open end of the needle. After the location of the tip of the injection needle has been ascertained, the needle body can be moved into communication with a container of medicant which is then expressed into the patient.

Frictional stops are provided to hold the injection needle in three specific positions during the injection procedure. In a first position, the open end of the injection needle is maintained out of communication with the sealed chamber and the container of injectible medication, while being inserted into the patient. In a second position, the open end of the injection needle is within the sealed chamber to facilitate welling up of blood into the container. In the third position, the open end of the needle is within the container of injectible medicant to allow expression of the medicant into the patient.

As has been disclosed in the earlier references cited above, there are particular advantages afforded by a disposable syringe with a collapsable container, as opposed to a hypodermic-type syringe. My present invention combines the advantages of the disposable syringe which employs a collapsable container, with the capability for determining the location of the tip of the injecton needle, to provide a unique dispensing device.

Accordingly, it is a primary object of this invention to provide a novel syringe preferably of the disposable type.

It is a further object of this invention to provide a disposable syringe adapted to automatically determine whether the injection needle has been inserted into a vein or artery of a patient.

It is a further object of this invention to provide a syringe wherein the injection needle is held by frictional stops in various specific positions to facilitate the administration of medical injectibles into a patient. Other objects and advantages of the present invention will be readily apparent to those skilled in the art by a reading of the following brief descriptions of the drawings, detailed description of the preferred embodiment, and the appended claims.

DESCRIPTION OF THE DRAWINGS

FIG. 1 is a perspective illustration of the disposable syringe;

FIG. 2 is a cross sectional view of the disposable syringe showing one of the alternate positions of this syringe in phantom;

FIG. 3 is a cross sectional view of the disposable syringe illustrated in position to dispense medicant.

FIG. 4 is a cross sectional view of the disposable syringe in communication with a mixing syringe.

DETAILED DESCRIPTION OF THE PREFERRED EMBODIMENT

Referring now to the drawings in detail, reference is first made to FIG. 1, wherein there is illustrated a disposable syringe in accordance with this invention, generally designated by numeral 100. The syringe 100 includes a flexible wall collapsable container 120, a needle housing assembly 101 with a transparent window 102, a needle carrier 150 and injection needle 151. As shown in FIGS. 2 and 3, protective end cap assembly 160, shown in phantom in FIG. 3, is threaded onto needle carrier 150.

A medicine, serum or the like 130 is provided inside the tubular container 120 as illustrated in FIG. 2. The liquid or other dispensable product 130 is normally present in the container 120 in a slight vacuum or negative pressure and is sealed against bacterial communication from outside the container 120. The overall operation of the dispensing device will now be outlined with reference to FIGS. 2 and 3.

The person administering a medical injection prepares a disposable syringe 100 for use by first removing the protective covering 160 which is threaded onto needle carrier 150. The needle carrier is at that time at its most outward position as illustrated in FIG. 2. Grasping the syringe by needle carrier 150, the needle is then inserted into the patient. The syringe assembly 100 is then moved into the configuration shown in phantom in FIG. 2. In this position, the open end of injection needle 151 has penetrated the sealed orifice 111 and is within the sealed lower pressure chamber 110. This application of a lower pressure differential to the open end of the needle allows blood to well up into the syringe and to be entrapped in sealed chamber 110, if the tip of the needle has lodged in a vein or artery of the patient. The person administering the injection can observe the result of moving the needle from position one to position two by looking through transparent opening 102.

Frictional stops are located within the needle carrier assembly, to allow for a positive fricitional engagement in specific positions. Frictional stop 104, FIGS. 2 and 3, facilitates insertion of the needle into the patient. Frictional stop 103 maintains the needle assembly in position to allow blood to well up into the syringe.

After it has been determined that the tip of the injection needle is in the desired location, needle carrier 150 is moved into the third position illustrated in FIG. 3. In this position, the open end of the needle 151 has penetrated a second sealable orifice and is within container 120. Medication 130 can then be expressed into the patient by collapsing the container, expressing the medicant through injection needle 151 into the patient. After the injection has been completed, the syringe is withdrawn from the patient and disposed of.

It will be noted that in the event the tip of the needle is not initially located properly, the process can be repeated until the person administering the injection is satisfied that the tip is properly located. Of course, after the seal to the sealed chamber has been violated, the lower presure differential within the chamber will begin to equalize, and there are a limit to the number of times that the tip of the needle can be relocated before the sealed chamber pressure is equal to atmospheric.

There are times when it may be desirable to mix the medicants to be expressed into the patient immediately before inoculation. To facilitate this as described in considerably more detail in my application Ser. No. 577,324 of which this application is a continuation-in-part, a mixing syringe can be inserted through injection needle 151 as shown in FIG. 4. As illustrated, injection needle 251 passes through neoprene or rubber seals 111 and 112 and extends into container 120. After the mixing has been completed, needle 251 is withdrawn from communication with disposable syringe assembly 100.

As illustrated, sealed chamber 110 is shown as a separate container within needle carrier assembly 101. In a preferred embodiment this sealed chamber 110 is constructed of a transparent material. But it will be appreciated that other configurations then those illustrated might be employed. For example, the sealed compartment could be manufactured as an integral unit with needle carrier assembly 101 and evacuated by some suitable means after manufacture. It will be further noted that the open end of needle 151 is adapted to pierce frangible seals 111 and 112 which may be constructed of any suitable material, such as rubber or neoprene.

As described above, transparent window 102 allows the person administering the injection to observe the contents of sealed chamber 110. Of course, it would be possible to construct sealed chamber 110 and needle housing assembly 101 entirely of transparent materials, such as glass or plastic, in which instance a transparent window would not be necessary.

Even further, it will be understood that various other constructions may be used to embody the concept of the present invention, within the spirit or scope of the claims and as is elsewhere recited as being objectives of the present invention.

It will be apparent from the foregoing that the various objectives of the present invention will be fulfilled.

I claim:
1. A syringe for medical injectibles comprising:
a flexible container to maintain the injectibles prior to injection into a patient;
a needle housing assembly maintained in fixed relation to the container;
a sealed chamber within the needle housing;
an injection needle having an interior cavity, a first end adapted to be inserted into a patient, and a second end adapted to pierce a sealable orifice, slideably disposed on a needle carrier assembly within said needle housing;
a first sealable orifice to allow communication between the interior cavity of the injection needle and the container when the second end of the injection needle is within the container;
a second sealable orifice to allow communication between the interior cavity of the injection needle and the sealed chamber when the second end of the injection needle is within the sealed chamber;
a first frictional stop to hold the injection needle in a first initial position for insertion into a patient in such a manner that the second end of the injection needle is not within the container or the sealed chamber;
a second frictional stop to hold the injection needle in a second position wherein the second end of the injection needle is within the sealed chamber.

* * * * *